United States Patent [19]

Fukui et al.

[11] Patent Number: 5,124,235
[45] Date of Patent: Jun. 23, 1992

[54] PHOTOPOLYMERIZATION INITIATOR AND PHOTOSENSITIVE COMPOSITION EMPLOYING THE SAME

[75] Inventors: Tetsuro Fukui, Kawasaki; Kyo Miura, Yokohama; Yoshio Takasu, Tama, all of Japan

[73] Assignee: Canon Kabushiki Kaisha, Tokyo, Japan

[21] Appl. No.: 758,714

[22] Filed: Sep. 9, 1991

Related U.S. Application Data

[62] Division of Ser. No. 385,070, Jul. 25, 1989, abandoned.

Foreign Application Priority Data

Jul. 26, 1988 [JP] Japan .................. 63-184594

[51] Int. Cl.$^5$ .............................. G03C 1/735
[52] U.S. Cl. ........................ 430/281; 430/325; 430/914; 522/12; 522/29; 522/66; 522/913
[58] Field of Search ............ 522/66, 12, 913, 29; 430/281, 325, 914, 280

[56] References Cited

U.S. PATENT DOCUMENTS

| | | | |
|---|---|---|---|
| 3,096,370 | 7/1963 | Bloom | 546/13 |
| 4,307,182 | 12/1981 | Dalzell et al. | 430/339 |
| 4,450,227 | 5/1984 | Holmes et al. | 430/339 |
| 4,865,942 | 9/1989 | Gottschalk et al. | 430/914 |
| 4,950,581 | 8/1990 | Koike et al. | 430/915 |
| 4,954,414 | 9/1990 | Adair et al. | 522/29 |
| 4,971,891 | 11/1990 | Kawamura et al. | 430/915 |

FOREIGN PATENT DOCUMENTS

| | | |
|---|---|---|
| 0224587 | 5/1987 | European Pat. Off. . |
| 384826 | 5/1973 | U.S.S.R. .................. 556/7 |

OTHER PUBLICATIONS

Borden, "Review of Light-Sensitive Tetraarylborates", Photographic Science and Engineering, vol. 16, No. 4, Aug. 1972, pp. 300-312.

*Primary Examiner*—Marion E. McCamish
*Assistant Examiner*—Christopher D. Rodee
*Attorney, Agent, or Firm*—Fitzpatrick, Cella, Harper and Scinto

[57] ABSTRACT

A photopolymerization initiator comprises a borate salt represented by the general formula (I):

$$M^{n\oplus}(B^{\ominus}R^1R^2R^3R^4)_n$$

wherein $R^1$, $R^2$, $R^3$, and $R^4$ are respectively any one of halogen atoms, alkyl radicals, alkenyl radicals, alkynyl radicals, alicyclic radicals, aryl radicals, aryloxyl radicals, alkoxyl radicals, aralkyl radicals, and heterocyclic radicals, and may be the same with or different from each other; $R^1$ and $R^2$, or $R^2$ and $R^3$ may be linked to form a ring; M is an atom of a metal selected from Groups IB, IIB, IIIA, and IVA of the periodic table; and n is an integer of 1 or 2.

A photosensitive composition comprises at least a polymerization compound and a photopolymerization initiator represented by the above general formula (I).

10 Claims, No Drawings

PHOTOPOLYMERIZATION INITIATOR AND PHOTOSENSITIVE COMPOSITION EMPLOYING THE SAME

This application is a division of application Ser. No. 07/385,070 filed Jul. 25, 1989, now abandoned.

BACKGROUND OF THE INVENTION

1. Field of the Invention

The present invention relates to a novel photopolymerization initiator and a photosensitive composition employing the same, and particularly to a novel photopolymerization initiator comprising a borate salt, and a photosenstive composition employing the same.

2. Related Background Art

A diversity of compounds are known as photopolymerization initiators: such as azo compounds, organic sulfur compounds, carbonyl compounds, and oxidation-reduction systems employing ferric ion. At present, most generally used ones are organic carbonyl compounds which are advantageous in that the sensivity thereof is relatively high, and the compounds are stable, and easily synthesized. The compounds, however, are limited in the application wavelengths up to 450 nm at the longest because the photosensitivity wavelength range thereof is equal to the absorption wavelength range of the compounds per se.

On the other hand, recently a combination of a pyrylium dye with a peroxide has enlarged the photosensitive range to long wavelength side. The combination, however, has a disadvantage of low storage stability which causes a short shelf life.

The need for photopolymerization initiators sensitive to longer wavelengths have resulted from the recent remarkable progress in laser technology. That is, the need has come from the desire to apply laser beams to recording processes such as resist patterning and photoengraving instead of using conventionally employed short wavelength light such as ultraviolet light. In particular, strongly desired are use of inexpensive and miniaturized semiconductor laser. The laser beam shorter than 650 nm, however, is considered not to be attainable. Under such circumstances, photopolymerization initiators have been extensively investigated which are sensitive to light of wavelength of 650 nm or longer.

Japanese Patent Laid-open Publication No. 62-143044 (1987), for example, discloses a photopolymerization initiator comprising a borate salt of a dye and having sensitivity at 500 nm or longer.

The initiator has disadvantages in that the synthesis of the compound is difficult and that the compound per se and the photosensitive composition derived therefrom are both unstable.

SUMMARY OF THE INVENTION

The object of the present invention is to provide a novel photopolymerization initiator which is free from the aforementioned disadvantages, sensitive to light of wavelengths of 500 nm or longer, highly stable, and easily synthesized, as well as a photosensitive composition containing the initiator.

According to an aspect of the present invention, there is provided a photopolymerization initiator comprising a borate salt represented by the general formula (I):

wherein $R^1$, $R^2$, $R^3$, and $R^4$ are respectively any one of halogen atoms, alkyl radicals, alkenyl radicals, alkynyl radicals, alicyclic radicals, aryl radicals, aryloxyl radicals, alkoxyl radicals, aralkyl radicals, and heterocyclic radicals, and may be the same or different from each other; $R^1$ and $R^2$, or $R^2$ and $R^3$ may be linked to form a ring; M is an atom of a metal selected from Groups IB, IIB, IIIA, and IVA of the periodic table; and n is an integer of 1 or 2.

According to another object of the present invention, there is provided a photosensitive composition containing a photopolymerization initiator represented by the general formula (I) shown above.

DETAILED DESCRIPTION OF THE PREFERRED EMBODIMENT

The photopolymerization initiator of the present invention is characterized in that the initiator is a borate salt represented by the general formula (I):

wherein $R^1$, $R^2$, $R^3$, and $R^4$ are respectively any one of halogen atoms, alkyl radicals, alkenyl radicals, alkynyl radicals, alicyclic radicals, aryl radicals, aryloxyl radicals, alkoxyl radicals, aralkyl radicals, and heterocyclic radicals, and may be the same or different from each other; $R^1$ and $R^2$, or $R^2$ and $R^3$ may be linked to form a ring; M is a counter cation atom and is a metal atom. n is an integer of 1 or 2.

In the present invention, the halogen atoms include fluorine atom, chlorine atom, bromine atom and iodine atom.

The alkyl radicals are preferably normal or branched alkyl radicals having 1 to 10 carbon atoms which may be substituted or unsubstituted, such as methyl, ethyl, propyl, isopropyl, butyl, isobutyl, t-butyl, amyl, isoamyl, octyl, trifluoromethyl, methoxymethyl, ethoxymethyl, methoxyisopropyl, ethoxypropyl, N,N-dimethylaminoethyl, N,N-dimethylaminopropyl and the like.

The alkenyl radical are preferably of 2 to 12 carbon atoms, such as vinyl, propenyl, butenyl, pentenyl, hexenyl, heptenyl, octenyl, dodecenyl, prenyl, and the like.

The alkynyl radicals are preferably of 2 to 10 carbon atoms, such as ethynyl, propargyl, butynyl, pentynyl, hexynyl, heptynyl, and the like.

The alicyclic radicals are preferably of 5 to 8 carbon atoms, such as cyclopentyl, cyclohexyl, cycloheptyl, cyclooctyl, and the like, and such radical may be substituted by alkyl or other radical.

The aryl radicals may be substituted or unsubstituted, and include such as phenyl, naphthyl, fluorophenyl, chlorophenyl, dichlorophenyl, methoxyphenyl, tolyl, xylyl, ethylphenyl, N,N-dimethylaminophenyl, chloronaphthyl, methoxynaphthyl, diphenylaminophenyl and the like.

The aryloxyl radicals includes phenoxy, naphthoxy, benzodioxy, p-tolyloxy, and the like.

The alkoxyl radicals may be substituted or unsubstituted, and includes methoxy, ethoxy, propoxy, butoxy, isopropoxy, benzyloxy, 2-phenylethoxy, 2-methoxyethyloxy, 2-ethoxyethyloxy, and the like.

The aralkyl radicals may be substituted or unsubstituted, and include benzyl, phenetyl, α-naphthylmethyl, β-naphthylmethyl, p-methoxybenzyl, p-chlorobenzyl, and the like.

The heterocyclic radicals include pyridyl, quinolyl, lepidyl, methylpyridyl, furyl, thienyl, indolyl, pyrrolyl, carbazolyl, N-ethylcarbazolyl and the like.

M is a univalent or bivalent metal atom. In particular, the atoms from Groups IB, IIB, IIIA, and IVA have favorable properties. Especially preferable are metals that are not excessively stable as cation and are easily reduced on exposure, having the standard electrode potential of $-2.0$ V or higher at 25° C., such as Cu, Zn, Ag, Cd, Sn, Hg, and Pb. The standard electrode potentials of $Zn^{2+}$, $Cd^{2+}$, $Sn^{2+}$, $Pb^{2+}$, $Cu^{2+}$, $Ag^{+}$, and $Hg^{2+}$ are respectively $-0.763$ V, $-0.403$ V, $-0.136$ V, $-0.126$ V, $0.153$ V, $0.799$ V and $0.854$ V. Among them, Cu, Ag, and Hg are particularly preferable from the viewpoint of photosensitivity.

The specific examples of the borate anion are tetramethylborate, tetraethylborate, tetrabutylborate, triisobutylmethylborate, di-t-butyldibutylborate, trifluoromethyltrifluoroborate, tetra-n-butylborate, tetraphenylborate, tetra-p-chlorophenylborate, tetraaniseborate, triphenylbutoxyborate, trianisebutylborate, trianisebenzyloxyborate, triphenylmethylborate, triphenylethylborate, triphenylpropylborate, triphenyl-n-butylborate, triphenylhexylborate, trimesitylbutylborate, tritolylisopropylborate, triphenylbenzylborate, tetraphenylborate, tetrabenzylborate, triphenylphenethylborate, triphenyl-p-chlorobenzylborate, trimethallylphenylborate, tricyclohexylbutylborate, tri(phenylethenyl)butylborate, di(α-naphthyl)dipropylborate, diisobinocamphenyldiamylborate, etc. Among them, diphenyldibutylborate, trichlorophenylbutylborate, triphenylbutylborate, trianisebutylborate, tetraphenylborate, tetrachlorophenylborate and trifluoromethyltrifluoroborate are particularly preferable.

The borate anion of the photopolymerization initiator of the present invention can be prepared by a reaction of a boron compound such as triarylboron and boron trifluoride with a nucleophilic reagent such as a lithium compound and a Grignard reagent. These methods of the synthesis are described in the papers below:

Journal für Praktische Chemie, vol. 26 (1964), page 15,
Journal of American Chemical Society, vol. 93 (1971), page 1816,
Journal of American Chemical Society, vol. 90 (1968) page 5280,
Annalen der Chemie, vol. 618 (1958), page 31,
Annalen der Chemie, vol. 563 (1949), page 110,
Inorganic Chemistry, vol. 1 (1962), page 738,
Journal of Organic Chemistry, 1964, page 1971, and so forth.

The borate anion thus prepared is reacted with silver nitrate, cupric sulfate or the like in an aqueous solution to give the boron salt for the photopolymerization initiator of the present invention.

In the Examples described later, the borate anion is prepared in an aqueous solution. The synthesis may also be carried out in a medium containing a binder such as gelatin, carboxymethylcellulose, ethylcellulose, polyvinyl alcohol, etc. which will serve as a protecting colloid agent.

The polymerization initiator of the present invention has features of high moisture resistance and high storage stability because the initiator is composed of a metal borate such as Cu, Ag, or Hg salt of a boron-containing anion.

The addition of a sensitizer to the photopolymerization initiator of the present invention enables selection of the photosensitive wavelength range on photopolymerization. The employed sensitizing coloring material include cyanine dyes, merocyanine dyes, polymethine dyes having an anilino substutuent, azulene dyes, pyrylium dyes, triarylamine dyes, triarylmethane dyes, xanthene dyes, etc.

The polymerizable compounds employed with the aforementioned photopolymerization initiators are radical polymerizable compounds and/or cationic-polymerizable compounds having one or more unsaturated double bonds. Specifically these compounds include, univalent monomers such as styrene, methylstyrene, chlorostyrene, bromostyrene, methoxystyrene, dimethylaminostyrene, cyanostyrene, nitrostyrene, hydroxystyrene, aminostyrene, carboxystyrene, acrylic acid, methyl acrylate, ethyl acrylate, cyclohexyl acrylate, acrylamide, methacrylic acid, methyl methacrylate, ethyl methacrylate, propyl methacrylate, butyl methacrylate, phenyl methacrylate, cyclohexyl methacrylate, vinylpyridine, N-vinylpyrrolidone, N-vinylimidazole, 2-vinylimidazole, N-methyl-2-vinylimidazole, propyl vinyl ether, butyl vinyl ether, isobutyl vinyl ether, β-chloroethyl vinyl ether, phenyl vinyl ether, p-methylphenyl vinyl ether, p-chlorophenyl vinyl ether; bivalent monomers such as divinylbenzene, distyryl oxalate, distyryl malonate, distyryl succinate, distyryl glutarate, distyryl adipate, distyryl maleate, distyryl fumarate, distyryl β,β-dimethylglutarate, distyryl 2-bromoglutarate, distyryl α,α'-dichloroglutarate, distyryl terephthalate, di(acryloyloxyethyl)oxalate, di(acryloyloxypropyl) oxalate, di(acryloyloxyethyl) malonate, di(acryloyloxypropyl) malonate, di(acryloyloxyethyl) succinate, di(acryloyloxyethyl) glutarate, di(acryloyloxyethyl) adipate, di(acryloyloxyethyl) maleate, di(acryloyloxyethyl) fumarate, di(acryloyloxyethyl) β,β-dimethylglutarate, ethylenediacrylamide, propylenediacrylamide, 1,4-phenylenediacrylamide, 1,4-phenylenebis(oxyethylacrylate), 1,4-phenylenebis(oxymethylethyl acrylate), 1,4-bis(acryloyloxyethoxy)cyclohexane, 1,4-bis(acryloyloxymethylethoxy)cyclohexane, 1,4-bis(acryloyloxyethoxycarbamoyl)benzene, 1,4-bis(acryloyloxymethylethoxycarbamoyl)benzene, 1,4-bis(acryloyloxyethocycarbamoyl)cyclohexane, bis(acryloyloxyethoxycarbamoylcyclohexyl)methane, di(methacryloyloxyethyl) oxalate, di(methacryloyloxypropyl) oxalate, di(methacryloyloxyethyl) malonate, di(methacryloyloxypropyl) malonate, di(methacryloyloxyethyl) succinate, di(methacryloyloxypropyl) succinate, di(methacryloyloxyethyl) glutarate, di(methacryloyloxyethyl) adipate, di(methacryloyloxyethyl) maleate, di(methacryloyloxyethyl) fumarate, di(methacryloyloxypropyl) fumarate, di(methacryloyloxyethyl) β,β'-dimethylglutarate, 1,4-phenylenebis(oxyethyl methacrylate), 1,4-bis(methacryloyloxyethoxy)cyclohexane, acryloyloxyethoxyethyl vinyl ether, etc.; tervalent monomers such as pentaerythritol triacrylate, pentaerythritol trimethacrylate, pentaerythritol tri(hydroxystyrene), cyanuric acid triacrylate, cyanuric acid trimethacrylate, 1,1,1-trimethylolpropane triacrylate, 1,1,1-trimethylolpropane trimethacrylate, tri(acryloyloxyethyl) cyanurate, 1,1,1-trimethylolpropanetri(acryloyloxyethyl), tri(ethyl vinyl ether) cyanurate, a condensation product of 1,1,1-trimethylolpropane, tri(toluenediisocyanate) and hydroxyethyl acrylate, and a condensation product of 1,1,1-trimethylolpropanetri(hexanediisocyanate) and p-hydroxystyrene; quadrivalent monomers such as ethylentetracrylamide, a condensation product of propylenetetracrylamide and acrylic acid; and further compounds having radicals derived from a vinyl ether, epoxy, thiirane, spiroorthoesters, spiroorthorobonates, bicycloorthoesters, trioxanes, trisiloxanes, or trimethylene sulfides. These polymerizable compounds may be used singly or in combination of two or more compounds.

The photosensitive composition of the present invention is prepared by using preferably 0.01 to 30 parts, more preferably 0.1 to 15 parts of the photopolymerization initiator of the invention with 100 parts of the aforementioned polymerizable compounds.

An excessive amount of the photopolymerization initiator will not give high degree of polymerization of the polymerizable compounds, and will not give a sufficiently hardened polymerized image, while insufficient amount of the initiator will not practically bring about polymerization reaction.

It is desirable to add to the photosensitive composition a substance serving as an autoxidation agent or a chain transfer agent such as an amine type compound, a halogen type compound, an onium salt type compound, or a thiol type compound. Addition of 0.5 to 100 parts, preferably 3 to 30 parts of the above-mentioned compound to 10 parts of the photopolymerization initiator of the present invention will give a polymerization image with a high crosslinking density.

The specific examples of the amine type compounds are diethanolamine, triethanolamine, diethanolaniline, p-dimethylaminocyanobenzene, p-diethylaminocyanobenzene, methyl p-dimethylaminobenzoate, ethyl p-dimethylaminobenzoate, and ethyl p-diethylaminobenzoate.

The specific examples of the halogen type compounds are tetrabormomethane, tribromobutane, 2,4,6-tribromophenol, $\gamma,\gamma,\gamma$-trichloro-phenylpropane, 2,4,6-tris(trichloromethyl)triazine, and 2-(p-methoxyphenyl)-4,6-bis(trichloromethyl)-triazine.

The specific examles of the onium salt type compounds are aromatic iodonium salts, aromatic sulfonium salts and the like such as diphenyliodonium, 4,4'-dimethylphenyliodonium, 4,4'-di-ethyl diphenyliodonium, triphenylsulfonium, and diphenyl(p-phenylthiophenyl)-sulfonium having a counter anion of $SbF_6^\ominus$, $AsF_6^{63}$, $PF_6^\ominus$, or $BF_4^\ominus$.

The specific examples of the thiol type compounds are mercapto-aromatic compounds such as 2-mercaptobenzothiazole, 2-mercaptobenzoxazole, 2-mercaptobenzodiazole, 5-methyl-2-mercaptobenzoxazole, 5-methyl-2-mercaptobenzothiazole, and 5-ethoxy-2-mercaptobenzothiazole.

The photosensitive composition of the present invention may be shapeless or of a definite shape.

In addition to the above substances, there may be added a binder, a dye, a plasticizer, a thermal polymerization inhibitor, or the like.

The photosensitive composition of the present invention is useful also for inks and paints in addition to resist materials and engraving materials.

As described above, the photopolymerization initiator of the present invention comprises an easy-synthesizable borate salt, serving stably in a form of the compound itself and the photosensitive composition thereof, and being sensitive to light of wavelength of 500 nm or longer.

The present invention will be described by referring to the Examples.

SYNTHESIS EXAMPLE 1

Synthesis of silver diphenyldibutylborate

A Grignard reagent was prepared from 5 grams of magnesium and 34 grams of butyl bromide in 170 ml or dried tetrahydrofuran in a darkroom. Thereto a solution of 35 grams of diphenylchloroboron in 50 ml of dried tetrahydrofuran is gradually added dropwise. After one hour of reaction, 500 ml of aqueous 2N sodium hydroxide solution was added and agitation was continued for more 10 minutes. The organic layer was separated, and dehydrated over calcium chloride. Subsequently the solvent was distilled off to dryness under a reduced pressure. Thereto 600 ml of distilled water was added, and the solution was filtered and subjected to salting out. The resulting white precipitate was collected by filtration, and dried. The yield was 46 grams.

2.0 grams of the sodium diphenyldibutylborate was dissolved in 40 ml of water, and a solution of 1.1 grams of silver nitrate in 10 ml of water was added dropwise with stirring. After stirring for 30 minutes, the white precipitate was collected by filtration and dried. The yield was 2.5 grams.

SYNTHESIS EXAMPLE 2

Synthesis of silver trianisebutylborate 40 grams of trianiseboron was dissolved in 250 ml of dried benzene in a darkroom. 1.2 times equivalent of butyllithium solution in tetrahydrofuran was gradually added dropwise with stirring. After 2 hours of stirring, the solvent was evaporated off to concentrate the solution under reduced pressure. After left standing for 2 to 3 hours, the formed white precipitate was collected by filtration and dried. The yield was 37 grams.

2.0 grams of the lithium trianisebutylborate thus obtained was dissolved in 40 ml of water. 0.82 gram of silver nitrate solution in 10 ml of water was added thereto dropwise with stirring and cooling in an ice-water bath. After 30 minutes of stirring, the resulting white precipitate was collected by filtration, washed with water, and dried. The yield was 2.3 grams.

SYNTHESIS EXAMPLE 3

Synthesis of copper trianisebutylborate

In a darkroom, 2.0 grams of the lithium trianisebutylborate prepared in Synthesis example 2 was dissolved in 40 ml of water. A solution of 0.45 gram of cupric sulfate in 10 ml of water was added thereto with stirring at a room temperature. After 30 minutes of stirring, the precipitate formed was collected by filtration, washed with water and dried. The yield was 1.8 grams.

SYNTHESIS EXAMPLE 4

Synthesis of triphenylbutylmercury 2.0 grams of lithium triphenylbutylborate was dissolved in 50 ml of water. Thereto a solution of 1.1 grams of mercuric nitrate in 30 ml of water was added dropwise. It was stirred for 30 minutes. The formed precipitation was collected by filtration, washed with water and dried. The yield was 2.2 grams.

EXAMPLE 1

A photosensitive liquid having the composition below was prepared in a darkroom.
Trimethylolpropane triacrylate: 15 parts
Polymethyl methacrylate: 10 parts
Ethyl p-dimethylaminobenzoate: 0.6 part
Silver diphenyldibutylborate: 1.4 parts
NK-190 (made by Nippon Kanko Shikiso K.K.): 0.02 part
1,2-dichloroethane: 70 parts The liquid was applied on a surface-treated polyethylene terephthalate (PET) film of 37 μm thick with an applicator so as to give a dry film thickness of 4 μm. Further thereon, an overcoat layer of 3 μm thick of PVA (polyvinyl alcohol) was provided.

The photosensitivity test was conducted by exposure to light for 3 seconds with a 370 W xenon lamp through a filter for cutoff of shorter wavelength light below 500 nm and through a mask. The PVA layer was washed with water, and then subjected to an etching treatment for 1 minute in an ethanol bath to remove unexposed portion, leaving a polymer image.

EXAMPLE 2

A photosensitive liquid having the composition below was prepared:
1,6-bis[2-(acryloxy)acetoxy]hexane: 10 parts
Trimethylolpropane triacrylate: 5 parts
Polymethyl methacrylate: 10 parts
2-mercaptobenzoxazole: 0.6 part
Silver trianisebutylborate: 1.6 parts
Disperse Red: 2.0 parts
NK-1414 (made by Nippon Kanko Shikiso K.K.): 0.02 part
1,2-dichloroethane: 70 parts The liquid was applied on an aluminum plate which had been subjected to anode oxidation treatment so as to give a dry film thickness of 2 μm. Further thereon, an overcoat layer of 3 μm thick of PVA was provided.

The photosensivity test was conducted by exposure to light for 5 seconds with the same light source and the same filter as those employed in Example 1. The PVA layer was washed with water and then etched for 1 minute in an ethanol bath to remove unexposed portion, leaving a red picture image.

EXAMPLE 3

A photosensitive article was prepared and tested in the same manner as in Example 2 except that 1.8 parts of silver tetraphenylborate was used in place of 1.6 parts of silver trianisebutylborate. Exposure for 7 seconds gave an image.

EXAMPLE 4

In a darkroom, a photosensitive liquid was prepared which has composition below:

1,3-bis[2-(acryloxyacetoxy)ethoxycarbamoyl]benzene: 5 parts
Glycidyl acrylate: 2 parts
Pentaerithritol triacrylate: 8 parts
Polyethyl methacrylate: 12 parts
Ethyl p-dimethylaminobenzate: 0.5 part
Copper trianisebutylborate: 1.4 parts
NK-190 (made by Nippon Kanko Shikiso k.K.): 0.02 part
1,2-dichloroethane: 70 parts The liquid was applied on a surface-treated PET film of 37 μm thick so as to dry film thickness of 2 μm. Further thereon, an overcoat layer of 2 μm thick was provided. The photosensitivity test was conducted in the same manner as in Example 1. Exposure for 10 seconds gave a polymer image.

EXAMPLE 5

A photosensitive article was prepared and tested in the same manner as in Example 1 except that 1.7 parts of triphenylbutyl mercury was used in place of 1.4 parts of silver diphenyldibutylborate. Exposure for 7 seconds gave an image.

We claim:

1. A photosensitive composition comprising at least a polymerizable compound and a photopolymerization initiator represented by the general formula (I):

wherein $R^1$, $R^2$, $R^3$, and $R^4$ are respectively any one of halogen atoms, alkyl radicals, alkenyl radicals, alkynyl radicals, alicyclic radicals, aryl radicals, aryloxyl radicals, alkoxyl radicals, aralkyl radicals, and heterocyclic radicals, and may be the same with or different from each other; $R^1$ and $R^2$, or $R^2$ and $R^3$ may be linked to form a ring; M is an atom of a metal selected from Groups IB, IIB, IIIA, and IVA of the periodic table; and n is an integer of 1 or 2.

2. The composition of claim 1, wherein said metal atom is of an element having a standard electrode potential of $-2.0$ volts or higher at 25° C.

3. The composition of claim 1, wherein said metal atom is selected from the group of Cu, Zn, Ag, Cd, Sn, Hg, and Pb.

4. The composition of claim 1, wherein said metal atom is selected from the group of Cu, Ag, and Hg.

5. The composition of claim 1, wherein said composition contains 0.01 to 30 parts by weight of said photopolymerization initiator per 100 weight parts of said polymerizable compound.

6. The composition of claim 1 wherein said composition further contains an autoxidation agent or a chain transfer agent.

7. A method for forming an image comprising irradiating a photosensitive composition with light having a wavelength of 500 nm or longer to form a polymer image, said composition comprising at least a sensitizing coloring matter, a polymerizable compound and a photopolymerization initiator represented by the general formula (I):

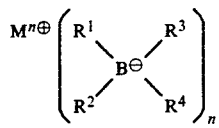

wherein $R^1$, $R^2$, $R^3$ and $R^4$ are each the same or different and are halogen atoms, alkyl radicals, alkenyl radicals, alkynyl radicals, alicyclic radicals, aryl radicals, aryloxyl radicals, alkoxyl radicals, aralkyl radicals, and heterocyclic radicals, $R^1$ and $R^2$, or $R^2$ and $R^3$ may be combined to form a ring; M is an atom of metal selected from Groups IB, IIB, IIIA, and IVA of the periodic table; and n is an integer of 1 or 2.

8. A method for forming an image of claim 7, wherein said metal atom is of an element having a standard electrode potential of $-2.0$ volts or higher at 25° C.

9. A method for forming an image of claim 7, wherein said metal atom is selected from the group of Cu, Zn, Ag, Cd, Sn, Hg, and Pb.

10. A method for forming an image of claim 7, wherein said metal atom is selected from the Group of Cu, Ag, and Hg.

* * * * *

UNITED STATES PATENT AND TRADEMARK OFFICE
CERTIFICATE OF CORRECTION

PATENT NO. : 5,124,235
DATED : June 23, 1992
INVENTOR(S) : TETSURO Fukui, et al

It is certified that error appears in the above-identified patent and that said Letters Patent is hereby corrected as shown below:

IN [57] ABSTRACT

Line 1  "merization" should read --merizable--.

COLUMN 2

Line 54, "radical" should read --radicals--.

COLUMN 3

Line 3, "includes" should read --include--.
Line 6, "includes" should read --include--.

COLUMN 4

Line 54, "(acryloyloxyethocycarbamoyl)" should read --(acryloyloxyethoxycarbamoyl)--.

COLUMN 5

Line 46, "tetrabormomethane," should read --tetrabromomethane,--.
Line 50, "examles" should read --examples--.
Line 55, "$AsF_6^{63}$" should read --$AsF_6^{\ominus}$--.

COLUMN 6

Line 18, "or" should read --of--.
Line 24, "more 10 minutes." should read --10 minutes more.--.

UNITED STATES PATENT AND TRADEMARK OFFICE
CERTIFICATE OF CORRECTION

PATENT NO. : 5,124,235

DATED : June 23, 1992

INVENTOR(S) : TETSURO FUKUI, ET AL

It is certified that error appears in the above-identified patent and that said Letters Patent is hereby corrected as shown below:

COLUMN 8

Line 12, "to dry" should read --to give a dry--.

Signed and Sealed this

Sixteenth Day of November, 1993

BRUCE LEHMAN

Attesting Officer   Commissioner of Patents and Trademarks